United States Patent
Kurz et al.

(10) Patent No.: US 6,306,905 B1
(45) Date of Patent: Oct. 23, 2001

(54) STABLE AQUEOUS FORMULATION OF 3-(N-BUTYLACETAMINO)-PROPIONIC ACID ETHYL ESTER

(75) Inventors: Thekla Kurz, Darmstadt; Sabine Hitzel, Messel; Dorothee Wille; Mohammad Jalalian, both of Darmstadt, all of (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/297,358

(22) PCT Filed: Oct. 22, 1997

(86) PCT No.: PCT/EP97/05826

§ 371 Date: Jul. 23, 1999

§ 102(e) Date: Jul. 23, 1999

(87) PCT Pub. No.: WO98/19537

PCT Pub. Date: May 14, 1998

(30) Foreign Application Priority Data

Nov. 2, 1996 (DE) .............................. 196 45 250

(51) Int. Cl.$^7$ .......................... A01N 37/46; A01N 37/12; A01N 25/22; A01N 25/00

(52) U.S. Cl. .......................... 514/551; 514/546; 514/769; 514/772; 514/784; 514/788; 514/919; 514/937; 514/944; 514/970; 514/971; 514/972; 424/405; 424/DIG. 5; 424/DIG. 10

(58) Field of Search ...................................... 514/547, 551, 514/919, 970, 972, 546, 769, 772, 784, 788, 937, 944, 971; 424/405, DIG. 5, DIG. 10

(56) References Cited

U.S. PATENT DOCUMENTS

| | | | |
|---|---|---|---|
| 4,127,672 | * 11/1978 | Klier et al. | 514/546 |
| 5,672,337 | 9/1997 | Ascione et al. | 424/59 |

FOREIGN PATENT DOCUMENTS

| | | |
|---|---|---|
| 3220884 | 12/1983 | (DE) . |
| 3220885 | 12/1983 | (DE) . |
| 0717982 | 6/1996 | (GB) . |

OTHER PUBLICATIONS

Insect Repellent 3535 pamphlet, unknown.*
The Merck Index, 10th edition, Merck & Co., Inc., NJ, p. 1395, item 9575, 1983.*
Marchio, F. "Insect Repellent 3535," SÖFW–Journal, vol. 122(7), pp. 478–485, 1996.*

* cited by examiner

Primary Examiner—John Pak
(74) Attorney, Agent, or Firm—Millen, White, Zelano & Branigan, P.C.

(57) ABSTRACT

The present invention relates to stable aqueous formulations of the insect repellent ethyl 3-(N-butyl-acetamino) propionate.

11 Claims, No Drawings

STABLE AQUEOUS FORMULATION OF 3-(N-BUTYLACETAMINO)-PROPIONIC ACID ETHYL ESTER

This application is a 371 of a PCT/EP97/05826, filed on Oct. 22, 1997.

The present invention relates to a stable aqueous formulation of the substance ethyl 3-(N-butyl-acetamino) propionate.

As is known, the substance ethyl 3-(N-butyl-acetamino) propionate has an insect-repelling action and is also used in this role. The insect repellent can be obtained commercially, for example from Merck KGaA, Darmstadt.

For people, insects are an annoyance or even a threat in a number of respects. As well as the damage caused by some types of insects (for example the destruction of whole harvests), people and many animals alike are annoyed, stung and otherwise troubled in one way or another by a large variety of insects. This can lead to infections and to the transmission of dangerous diseases.

The main weapons in the fight against insects are insecticides, although their use and toxicity profile are not always without problems. Measures such as the use of insect eradicators are, however, not necessarily required to prevent direct annoyance.

Since nowadays environmental protection is very much at the fore, preventive measures are preferably used.

Thus insect repellents are now likely to be preferred to insecticides for controlling insects, since the former are merely intended to prevent insects from settling on a host.

The requirements for an insect repellent are high and manifold. Above all, effective protection of the skin against insects must be ensured. Lasting repellency over a number of hours, even under climatically unfavourable conditions, is important. The repellent should have as broad an activity spectrum as possible.

Other requirements are maximum skin and mucosa compatibility without toxic, allergenic or sensitizing properties, although there should be no penetration of the skin.

In addition, the substance should have high chemical stability, i.e. should not undergo hydrolysis or (photo) oxidation, high thermal stability and high perspiration resistance.

Furthermore, an insect repellent must be readily compatible and miscible with common cosmetic and pharmaceutical formulation bases.

The insect repellent ethyl 3-(N-butyl-acetamino) propionate satisfies this multiplicity of requirements.

It has however been established that this substance is degraded in aqueous formulations during the storage period. This degradation is speeded up under the influence of elevated temperatures. Even a temperature increase of 10° C. can double the rate of degradation.

This must be considered a disadvantage, since it is often the case that corresponding insect repellent formulations are stored for years after their manufacture and sale, or are only used now and again over a long period. In addition, higher temperatures (certainly 50° C. and above) are frequently encountered during the storage of cosmetic formulations in summer, especially in southern countries. It is thus possible that the insect repellent will already have been so severely degraded that its effect is considerably diminished.

It therefore appears desirable to provide aqueous or hydrous formulations of improved stability which have an unchanged content of ethyl 3-(N-butyl-acetamino) propionate over a long period, even at elevated temperatures.

Surprisingly, it has been found that the stability of aqueous formulations comprising ethyl 3-(N-butylacetamino)propionate can be considerably increased if formulations having a higher pH, preferably buffered solutions, are used.

Base formulations for cosmetic or pharmaceutical preparations are often prepared on the basis of aqueous alcoholic solutions. Such formulations are also known in connection with the insect repellent ethyl 3-(N-butylacetamino) propionate. However, there are no indications at all in the literature that formulations having a higher pH, in particular buffered formulations, are being used to improve stability.

The invention provides a stable aqueous formulation of the insect repellent ethyl 3-(N-butylacetamino)propionate which is characterized in that solutions having a higher pH, preferably buffered solutions, are used for stabilization.

The pH of these solutions is in a pH range greater than 3.0, preferably in the range from 3.5 to 7.9. In addition to acids and bases, such as, for example, citric acid or sodium hydroxide solution, buffers can also be used for adjusting the pH.

Suitable buffer system include any known buffer solutions in this pH range. Such buffers are generally known to the person skilled in the art and require no further explanation here.

According to the invention, a buffer selected from the following group of buffer systems is preferred. This group of buffer systems is merely given by way of example and is in no way limiting with respect to the formulations according to the invention: citric acid/disodium hydrogenphosphate, effective in a pH range from 2.2 to 7.8 (preferably 0.1 M citric acid/0.2 M $Na_2HPO_4$), tris(hydroxymethyl) aminomethane/HCl, effective in the pH range around 7.2 to 9.0 (preferably 0.2 M/0.1 M), disodium citrate/HCl, effective in the pH range from 1.2 to 5.0 (preferably 0.1 M/0.1 M), potassium hydrogenphthalate/NaOH, effective in the pH range from 4.2 to 6.2 (preferably 0.1 M/0.1 M), disodium citrate/NaOH, effective in the pH range from 5.2 to 6.6 (preferably 0.1 M/0.1 M), potassium dihydrogenphosphate/disodium hydrogenphosphate, effective in the pH range from 5.0 to 8.0 (preferably both 1/15 mol/l), or also triethanolamine+Titriplex III/HCl, effective in the pH range from 7.0 to 8.8 (preferably 0.5 mol/l/0.05 mol/l).

The invention also provides for the use of solutions adjusted or buffered using, for example, citric acid or sodium hydroxide solution for stabilizing hydrous formulations of the insect repellent ethyl 3-(N-butylacetamino)propionate. The pH of these solutions is in the range greater than 3.0. The pH is preferably in the range from 3.5 to 7.9.

Examples of suitable hydrous formulations are, inter alia, lotions, emulsions, like cream or milk (W/O or O/W), gels and also solid sticks.

In addition to other additives, UV filters can also be incorporated into these hydrous formulations, giving sunscreens or UV-protection formulations which can be applied to the skin and, if desired, also to the hair. Examples of suitable UV filters obtainable commercially are, inter alia, Eusolex 6300®, Eusolex 4300®, Eusolex 9020®, Eusolex 232®, Eusolex 2292®, Eusolex OCR®, Eusolex HMS®, Eusolex 6007®, PABA and Uvinul T 150®. UV filters can be incorporated individually or in combination with others into the formulations according to the invention in concentrations of from 0.5 to 10% by weight.

An emulsion according to the invention in the form of an insect repellent cream or milk can, in addition to the insect-repelling substance ethyl 3-(N-butylacetamino) propionate in solution or in solution with a suitable buffer, further comprise for example the following substances: fatty alcohols, fatty acid esters, fatty acids, lanolin, natural or synthetic oils or waxes and emulsifiers in the presence of water.

Lotions according to the invention comprise, inter alia, natural or synthetic oils and waxes, lanolin, fatty acid esters, low molecular weight alcohols or polyols.

Most gels further comprise thickeners, such as, for example, silica.

The solid sticks consist of natural or synthetic waxes and oils, fatty alcohols, fatty acids, fatty acid esters and lanolin in addition to the additives according to the invention.

The formulations according to the invention can also be in the form of aerosols, in which case the usual propellants, such as alkanes, fluoroalkanes and fluorochloroalkanes, are used as a rule.

The composition and preparation of such hydrous formulations are generally known to the person skilled in the art and require no further explanation here.

In another preferred embodiment, the pH in the formulations according to the invention is in the range from 4.5 to 8.0, and a particularly strong stabilization effect is displayed by formulations having a pH between 6.5 and 7.9.

The content of ethyl 3-(N-butylacetamino)-propionate in the formulations according to the invention is 1 to 50% by weight, preferably 10 to 30% by weight.

The formulations according to the invention are prepared simply by mixing the individual components with stirring.

The provision of the formulations according to the invention makes available aqueous or hydrous formulations of ethyl 3-(N-butylacetamino)propionate which have an unchanged content of this substance over a long period. Even at high storage temperatures of from 30° to above 40° C. there is practically no decomposition with the preferred higher pH values.

Even without further elaboration, it is assumed that a person skilled in the art can utilize the above description to the full extent. The preferred embodiments are therefore merely to be seen as a descriptive disclosure which is in no way limiting.

The complete disclosure contents of all applications, patents and publications cited above and below are incorporated herein by reference.

For clarification and illustration, examples are given below which are within the scope of the present invention, but which are not intended to limit the invention to these examples.

EXAMPLE 1

Using the buffer system 0.1 M citric acid/0.2 M sodium sulfate, solutions of pH 3.5, 4.4 and 6.5 are prepared by simply mixing the components with stirring. This buffer system can thus be effective over a broad pH range.

a) A solution of pH 3.5 having the following composition (in % by wt.) is prepared:

| | | |
|---|---|---|
| Ethyl 3 - (N-butylacetamino)propionate (Art. No. 111887) | (1) | 10.0% |
| 96% ethanol (Art No. 100971) | (1) | 15.0% |
| Buffer pH 3.0 | | ad 100.0% | b) A solution of pH 4.4 having the following composition (in % by wt.) is prepared:

| | | |
|---|---|---|
| Ethyl 3 - (N-butylacetamino)propionate (Art. No. 111887) | (1) | 10.0% |
| 96% ethanol (Art No. 100971) | (1) | 15.0% |
| Buffer pH 4.0 | | ad 100.0% | c) A solution of pH 6.5 having the following composition (in % by wt.) is prepared:

| | | |
|---|---|---|
| Ethyl 3 - (N-butylacetamino)propionate (Art. No. 111887) | (1) | 10.0% |
| 96% ethanol (Art No. 100971) | (1) | 15.0 |
| Buffer pH 6.0 | | ad 100.0% |
| Source of supply: (1) Merck KGaA, Darmstadt | | |

EXAMPLE 2

Using the buffer system 0.2 M tris(hydroxymethyl) aminomethane/0.1 M HCl, a solution of pH 7.9 is prepared by mixing the following components with stirring (amounts in % by wt.)

| | | |
|---|---|---|
| Ethyl 3 - (N-butylacetamino)propionate (Art. No. 111887) | (1) | 10.0% |
| 96% ethanol (Art No. 100971) | (1) | 15.0% |
| Buffer pH 8.0 | | ad 100.0% |
| Source of supply: (1) Merck KGaA, Darmstadt | | |

Example A

The stability of ethyl 3-(N-butylacetamino)-propionate was tested in buffered solutions as a function of pH. The aqueous formulations according to the invention, prepared as in Examples 1 and 2, were subjected to a storage test over 12 months both at room temperature and at 40° C.

The results are given in Tables 1 and 2.

TABLE 1

| pH of the buffered solution | Storage at room temperature [months] | | | | |
|---|---|---|---|---|---|
| | 0 | 3 | 6 | 9 | 12 |
| | repellent content in % | | | | |
| 3.5 | 10.1 | 8.8 | 8.0 | 7.2 | 6.4 |
| 4.5 | 10.2 | 9.8 | 9.6 | 9.4 | 9.0 |
| 6.5 | 10.2 | 9.8 | 9.7 | 9.6 | 9.3 |
| 7.9 | 10.2 | 9.7 | 9.6 | 9.7 | 9.5 |

TABLE 2

| pH of the buffered solution | Storage at room temperature [months] | | | | |
|---|---|---|---|---|---|
| | 0 | 3 | 6 | 9 | 12 |
| | repellent content in % | | | | |
| 3.5 | 10.1 | 5.8 | 3.5 | 2.8 | 2.7 |
| 4.5 | 10.2 | 8.2 | 7.0 | 5.3 | 4.0 |
| 6.5 | 10.2 | 9.3 | 8.5 | 7.8 | 6.8 |
| 7.9 | 10.2 | 9.6 | 9.3 | 8.9 | 7.9 |

Example B

In this example, aqueous solutions of ethyl 3-(N-butylacetamino)propionate were subjected to a storage test at 40° C. as a function of pH. The corresponding aqueous solutions comprise the following:

Solution 1 (pH 4.5):

| | | in % by wt. |
|---|---|---|
| Ethyl 3 - (N-butylacetamino)propionate (Art. No. 111887) | (1) | 10.0 |
| 96% ethanol (Art No. 100971) | (1) | 15.0 |
| NaCl (Art. No. 6400) | (1) | 0.1 |
| Water, demin. | | ad 100.0 |
| pH adjustment with hydrochloric acid | | |

Solution 2 (pH 6):

Composition as for solution 1; pH adjustment to pH 6 with sodium hydroxide solution.

Solution 3 (pH 8):

Composition as for solution 1; pH adjustment to pH 8 with sodium hydroxide solution. Source of supply: Merck KGaA, Darmstadt The results of the storage test of the different solutions are summarized in Table 3.

TABLE 3

| pH of the buffered solution | Storage at room temperature [months] | | | | |
|---|---|---|---|---|---|
| | 0 | 3 | 6 | 9 | 12 |
| | repellent content in % | | | | |
| (1) 4.5 | 9.9 | 4.4 | 2.7 | 2.2 | 2.5 |
| (2) 6.0 | 10.1 | 6.0 | 2.9 | 2.5 | 2.6 |
| (3) 8.0 | 10.0 | 8.6 | 3.0 | 2.5 | 2.6 |

A comparison of Tables 2 and 3 clearly shows that the insect repellent in the buffered formulations according to the invention is considerably more stable, and degradation is markedly slowed, in particular at higher pHs.

What is claimed is:

1. A stable aqueous formulation of the insect repellent ethyl 3-(N-butylacetamino) propionate, comprising ethyl 3-(N-butylacetamino) propionate in a buffered solution or buffer system having a pH of 3.5 or greater, selected from a group consisting of citric acid/$Na_2HPO_4$, tris (hydroxymethyl) amino-methane/HCl, disodium citrate/HCl, potassium hydrogen-phthalate/NaOH, disodium citrate/NaOH, potassium dihydrogenphosphate/disodium hydrogenphosphate, and triethanolamine and Titriplex III/HCl.

2. The formulation according to claim 1, wherein the pH is in a range of pH 3.5–7.9.

3. The formulation according to claim 1, wherein the insect repellent is in a concentration of 1% by weight–50% by weight.

4. The formulation according to claim 3, wherein the concentration of insect repellent is 10–30% by weight.

5. The aqueous formulation according to claim 1, further comprising one or more UV filters in a concentration of 0.5–10% by weight.

6. The aqueous formulation according to claim 1 in the form of a lotion, emulsion, cream or milk, gel or solid stick.

7. The formulation of claim 1, wherein the pH is 4.5 or greater.

8. A method of repelling insects, comprising applying to a subject a stable aqueous formulation of an insect repellent containing ethyl 3-(N-butylacetamino) propionate, which is buffered at a pH at least 3.5 by a buffer system, wherein said buffer system is citric acid/$Na_2HPO_4$, tris(hydroxymethyl) aminomethane/HCl, disodium citrate/HCl, potassium hydrogenphosphate or triethanolamine and Titriplex III/HCl.

9. The method according to claim 8, wherein the pH of the solution is pH 3.5–7.9.

10. The method according to claim 8, wherein the insect repellent is in a concentration of 1% by weight–50% by weight.

11. The method of claim 10, wherein the concentration of insect repellent is 10–30% by weight.

* * * * *

UNITED STATES PATENT AND TRADEMARK OFFICE
CERTIFICATE OF CORRECTION

PATENT NO.    : 6,306,905 B1
DATED         : October 23, 2001
INVENTOR(S)   : Kurz et al.

It is certified that error appears in the above-identified patent and that said Letters Patent is hereby corrected as shown below:

<u>Title page, Item [54] and Column 1, lines 1-3,</u>
Please delete the title and insert the new title -- STABLE AQUEOUS FORMULATION OF ETHYL-3-(N-BUTYLACETAMINO)-PROPIONIC ACID ETHYL ESTER --

Signed and Sealed this

Thirty-first Day of December, 2002

JAMES E. ROGAN
*Director of the United States Patent and Trademark Office*